US009316578B2

(12) United States Patent
Grier et al.

(10) Patent No.: US 9,316,578 B2
(45) Date of Patent: Apr. 19, 2016

(54) AUTOMATED REAL-TIME PARTICLE CHARACTERIZATION AND THREE-DIMENSIONAL VELOCIMETRY WITH HOLOGRAPHIC VIDEO MICROSCOPY (75) Inventors: David G. Grier, New York, NY (US); Fook Chiong Cheong, Singapore (SG); Ke Xiao, Elmhurst, NY (US)

(73) Assignee: New York University, New York, NY (US)

( * ) Notice: Subject to any disclaimer, the term of this patent is extended or adjusted under 35 U.S.C. 154(b) by 624 days.

(21) Appl. No.: 13/254,403

(22) PCT Filed: Jan. 14, 2010

(86) PCT No.: PCT/US2010/021045
§ 371 (c)(1),
(2), (4) Date: Feb. 15, 2012

(87) PCT Pub. No.: WO2010/101671
PCT Pub. Date: Sep. 10, 2010

(65) Prior Publication Data
US 2012/0135535 A1    May 31, 2012

Related U.S. Application Data (63) Continuation-in-part of application No. 12/740,628, filed on Oct. 30, 2008.

(60) Provisional application No. 61/145,402, filed on Jan. 16, 2009, provisional application No. 61/171,199, filed on Apr. 21, 2009.

(51) Int. Cl.
*G01N 21/00* (2006.01)
*G01N 15/14* (2006.01)
*G01N 15/00* (2006.01)

(52) U.S. Cl.
CPC ........ *G01N 15/1475* (2013.01); *G01N 15/1484* (2013.01); *G01N 2015/003* (2013.01);
(Continued)

(58) Field of Classification Search
None
See application file for complete search history.

(56) References Cited

U.S. PATENT DOCUMENTS 3,069,654 A    12/1962    Hough
4,532,422 A    7/1985    Nomura et al.
(Continued)

FOREIGN PATENT DOCUMENTS

CA    1 159 674 A1    1/1984
EP    0 035 437    1/1986
(Continued)

OTHER PUBLICATIONS

Kolomenkin, M. et al. Geometric voting algorithm for star trackers, 2008, IEEE Transactions on Aerospace and Electronic Systems, vol. 44(2), pp. 441-456.*

(Continued)

*Primary Examiner* — Robert Xu
(74) *Attorney, Agent, or Firm* — Foley & Lardner LLP (57) ABSTRACT

An in-line holographic microscope can be used to analyze on a frame-by-frame basis a video stream to track individual colloidal particles' three-dimensional motions. The system and method can provide real time nanometer resolution, and simultaneously measure particle sizes and refractive indexes. Through a combination of applying a combination of Lorenz-Mie analysis with selected hardware and software methods, this analysis can be carried out in near real time. An efficient particle identification methodology automates initial position estimation with sufficient accuracy to enable unattended holographic tracking and characterization.

18 Claims, 8 Drawing Sheets

(52) U.S. Cl.
CPC  *G01N2015/1445* (2013.01); *G01N 2015/1454* (2013.01); *G01N 2015/1493* (2013.01); *G01N 2015/1497* (2013.01)

(56) References Cited

U.S. PATENT DOCUMENTS

| | | | |
|---|---|---|---|
| 4,627,729 | A | 12/1986 | Breuckmann et al. |
| 4,740,079 | A | 4/1988 | Koizumi et al. |
| 4,986,659 | A | 1/1991 | Bachalo |
| 4,998,788 | A | 3/1991 | Osakabe et al. |
| 5,095,207 | A | 3/1992 | Tong |
| 5,796,498 | A | 8/1998 | French |
| 5,880,841 | A | 3/1999 | Marron et al. |
| 6,281,994 | B1 | 8/2001 | Horikoshi et al. |
| 6,710,874 | B2 | 3/2004 | Mavliev |
| 7,248,282 | B2 | 7/2007 | Maddison |
| 8,119,988 | B2 | 2/2012 | Daido et al. |
| 2003/0021382 | A1 | 1/2003 | Iwanczyk et al. |

FOREIGN PATENT DOCUMENTS

| | | |
|---|---|---|
| EP | 0 278 714 | 8/1988 |
| JP | 55-096976 A | 7/1980 |
| JP | 3-251888 A | 11/1991 |
| JP | 2001-034148 A | 2/2001 |
| JP | 2005-0512127 A | 4/2005 |
| JP | 2007-279475 A | 10/2007 |
| WO | WO 03/048868 A1 | 6/2003 |
| WO | WO 2008/092107 A1 | 7/2008 |
| WO | WO 2008/127410 A2 | 10/2008 |
| WO | WO 2009/059008 A1 | 5/2009 |

OTHER PUBLICATIONS

Pawashe, C. et al. Two-dimensional vision-based autonomous microparticle manipulation using a nanoprobe, 2006, Journal of Micromechatronics, vol. 3(3-4), pp. 285-306.*

Denis et al., "Direct Extraction of the Mean Particle Size from a Digital Hologram", *Applied Optics*, Feb. 10, 2006, pp. 944-952, vol 45, No. 5, Optical Society of America.

Moreno et al., "Particle Positioning from Charge-Coupled Device Images by the Generalized Lorenz-Mie Theory and Comparison with Experiment", *Applied Optics*, Oct. 1, 2000, pp. 5117-5124, vol. 39, No. 28, Optical Society of America.

Sheng et al., "Digital Holographic Microscope for Measuring Three-Dimensional Particle distributions and Motions", *Applied Optics*, Jun. 1, 2006, pp. 3893-3901, vol. 45, No. 16, Optical Society of America.

JP Office Action (English Translation), Application No. 2011-546331, Oct. 25, 2012, 2 pages.

JP Preliminary Report of Issuance of Office Action, Application No. 2010-531335, Oct. 23, 2012, 4 pages.

Colomb, et al., "Polarization microscopy by use of digital holography: application to optical-fiber birefringence measurements", *Applied Optics*, Jul. 20, 2005, pp. 4461-4469, vol. 44, No. 21, Optical Society of America.

Lee, et al., "Characterizing and tracking single colloidal particles with video holographic microscopy", *Optics Express*, Dec. 24, 2007, pp. 18275-18282, vol. 15, No. 26, Optical Society of America.

Rappaz et al., "Simultaneous cell morphometry and refractive index measurement with dual-wavelength digital holographic microscopy and dye-enhanced dispersion of perfusion medium", *Optics Letters*, Apr. 1, 2008, pp. 744-746, vol. 33, No. 7, Optical Society of America.

Rappaz et al., "Erythrocytes volume and refractive index measurement with a Digital Hololgraphic Microscope", *Proc. of SPIE*, (2007), pp. 644509-1-644509-5, vol. 6445, Optical Diagnostics and Sensing VII.

Kao et al., "Tracking of Single Fluorescent Particles in Three Dimensions: Use of Cylindrical Optics to Encode Particle Position", *Biophysical Journal*, Sep. 1994, pp. 1291-1300, vol. 67, The Biophysical Society.

First Office Action with English Translation in Chinese Application No. 20108009712.X, dated Dec. 18, 2012, 21 pages.

Non-Final Office Action in U.S. Appl. No. 12/740,628, dated Jan. 17, 2013, 30 pages.

Lee, Sang-Hyuk et al., "Holographic Microscopy of Holographically Trapped Three-Dimensional Structures", *Optics Express*, (2007) pp. 1505-1512, Optical Society of America.

Japanese Office Action with English Translation dated Dec. 18, 2013, Japanese Application No. 201080009712.X, 21 pages.

Japanese Third Office Action with English Translation dated Apr. 2, 2014, Japanese Application No. 201080009712.X, 9 pages.

Office Action for U.S. Appl. No. 12/686,036 dated Mar. 27, 2012, 7 pages.

Notice of Allowance for U.S. Appl. No. 12/686,036 dated Aug. 6, 2012, 8 pages.

Notification of Fourth Office Action for Chinese App. No. 201080009712.X, dated Sep. 17, 2014, 3 pages.

* cited by examiner

Optical
FIG. 1C(1)

Fitted
FIG. 1C(2)

AUTOMATED REAL-TIME PARTICLE CHARACTERIZATION AND THREE-DIMENSIONAL VELOCIMETRY WITH HOLOGRAPHIC VIDEO MICROSCOPY

CROSS-REFERENCE TO RELATED PATENT APPLICATIONS

This application is a U.S. National Phase application based on PCT Application No.: PCT/US2010/021045, filed Jan. 14, 2010. PCT/US2010/021045 claims priority to U.S. Provisional Application No. 61/145,402, filed Jan. 16, 2009 and U.S. Provisional Application No. 61/171,199, filed Apr. 21, 2009. This application is also a continuation-in-part of co-pending U.S. patent application Ser. No. 12/740,628, filed Oct. 30, 2008. The contents of these applications are incorporated herein by reference in their entirety.

This work was supported by the National Science Foundation through Grant Number DMR-0606415. The U.S. Government has certain rights pursuant to this National Science Foundation Grant.

BACKGROUND OF THE INVENTION

This characterization of colloidal particles, particularly spheres, is an important and pervasive issue in many aspects of industrial chemical, physical and biomedical applications. A variety of important functionalities are being sought to perform various characterizations including 1) bead based molecular binding assays, 2) flow field measurements, 3) automated particle image detection in holograms, and 4) real time analysis of particle features. For example, coherent illumination traditionally has not been used widely for particle image velocimetry because the resulting holographic images can be difficult to interpret quantitatively. Consequently, measurements of fluoroscence yield has been used to carry out bead based molecular binding assays using holographic imaging in one color. However, such methods require fluorescent labeling with conventional assays requiring tens of thousands of beads to eliminate artifacts to non-specific fluorospore binding and unintentional bleaching. It has been recently demonstrated that holographic video microscopy images of colloidal particles can be used to locate the particles' centers in three dimensions, even when particles occlude each other along the optical axis. Earlier demonstrations using phenomenological models for the observed scattering patterns achieved tracking resolution comparable to that attained with conventional particle imaging methods. The principal benefit of coherent illumination in these studies was the greatly extended working distance and depth of focus compared with conventional imaging methods. However, these methods are inefficient, do not allow any real time analysis to be performed and cannot even perform a number of characterizations (such as the four listed above). Consequently, characterizations mentioned above have not been possible heretofore, have not been commercially feasible or problems remain without apparent solution.

SUMMARY OF THE INVENTION

In therefore an object of the invention to provide a variety of characterization methods and systems for analysis of colloidal particles, such as spheres, in an automated, real-time manner using holographic video microscopy.

BRIEF DESCRIPTION OF THE DRAWINGS

FIG. 6A(1) is a distribution of streaming particles as a function of index of refraction and observed sizes for a commercial polystyrene spherical particle continuing sample in water; FIG. 6A(2) is a 2D cross section from FIG. 6A(1) for the particle size and FIG. 6A(3) for index of refraction, both being at the mean value of the other parameter; FIGS. 6B(1) and 6B(2) show trajectory averaged radius and refractive index as a function of mean speed;

DESCRIPTION OF PREFERRED EMBODIMENTS

Figure 1A:
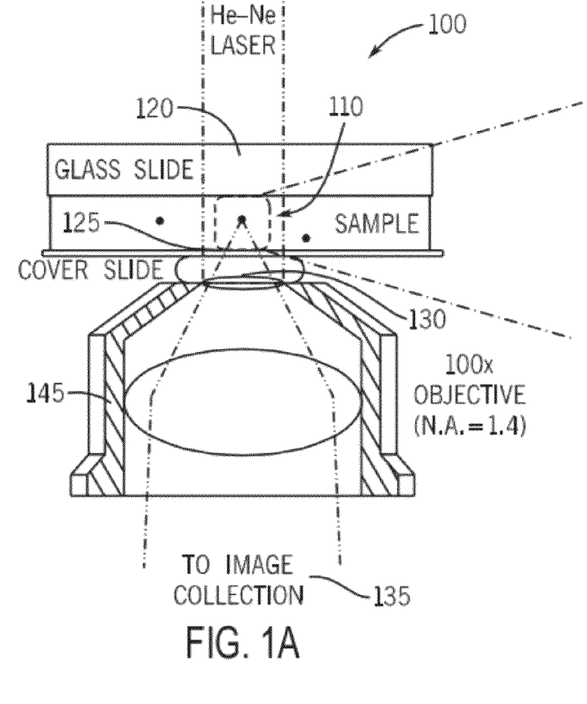
FIG. 1A shows an example of an in-line holographic video microscope.
Figure 1B:
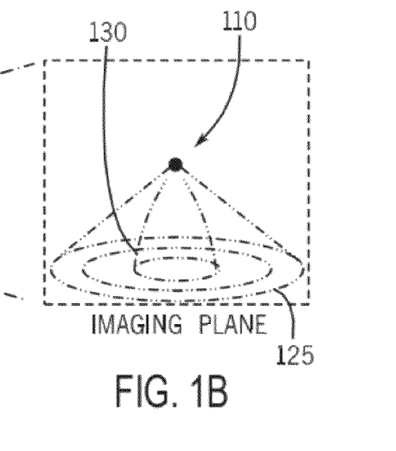
FIG. 1B is a magnified portion of FIG. 1A around the sample; an interference pattern is shown in FIG. 1C(1) and FIG. 1C(2) shows a fit of FIG. 1C(1) to predictions of Lorenz-Mie theory to obtain various measurements.
Figure 1C:
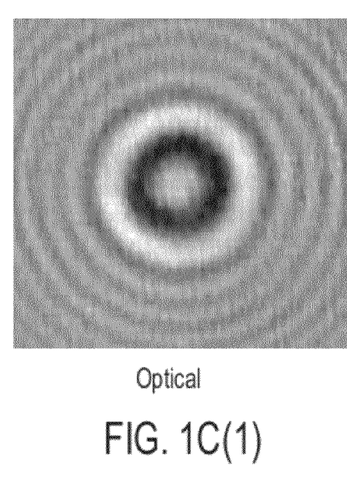

A holographic microscope 100 constructed for implementation of the invention is depicted schematically in FIG. 1A. Sample 110 is illuminated with the collimated and linearly polarized beam 120 from a HeNe laser operating at a vacuum wavelength of λ=632.8 nm (Uniphase 5 mW). Other laser wavelengths, such as λ=537 can also be employed (Coherent Verdi at 5 W). Light 130 scattered by the sample 110 interferes with the unscattered portion of the illuminating beam 120 to form an in-line hologram in the focal or imaging plane 125 of the microscope 100. The resulting heterodyne scattering pattern (see FIG. 1C(1)) is magnified by the microscope's objective lens 145 (Zeiss S Plan Apo 100× oil immersion, numerical aperture 1.4), and projected with a 1× video eyepiece onto a video camera 135 (or plural camera for some embodiments) (NEC TI-324AII), which records 1 ms exposures every 33 ms with a system magnification of 101 µm/pixel. As described hereinafter this scattering, or interference pattern, is fit to predictions of the Lorenz-Mie theory (see FIG. 1C(2)).

This video signal can be either recorded as an uncompressed digital video stream at 30 frames/s on a commercial digital video recorder (Pioneer H520S) for off-line analysis, or digitized directly with an Arvoo Picasso PCI-2SQ framegrabber to yield an eight-bit image, $A(r)$. Normalizing each image by a previously recorded background image, $B(r)$, eliminates spurious interference fringes due to reflections and imperfections in the optical train and provides the real-valued array $a(r)=a(r)/B(r)$ for analysis. In our implementation, each pixel in the 640/480 array contains roughly five bits of information.

We interpret the data in $a(r)$ using results for generalized Lorenz-Mie scattering theory. The electric field in the microscope's focal plane is the superposition of the incident plane wave, $E_0(r)=u_0(x,y)\exp(ikz)\hat{x}$, and the scattering pattern $E_s(r)=u_0(r_p)f_s(k(r-r_p))$ due to a sphere centered at $r_p$. There, $k=2\pi n_m/\lambda$ is the light's wavenumber in a medium of refractive index $n_m$. After normalization, $$a(r) \approx 1 + 2\Re\{\exp(-ikz_p)f_s(k(r-r_p))\cdot\hat{x}\} + |f_s(k(r-r_p))|^2. \quad (1)$$

The scattering function may be expanded in a series of vector spherical harmonics $$f_s(kr) = \sum_{n=1}^{n_c} f_n(ia_n N_{e1n}^{(3)}(kr) - b_n M_{o1n}^{(3)}(kr)),$$

where $f_n = i^n(2n+1)/[n(n+1)]$. The generalized Lorenz-Mie expansion coefficients, $a_n$ and $b_n$, depend on the size, shape, composition and orientation of the scattering particle in the illuminating field. For a homogeneous isotropic sphere of radius a illuminated by a plane wave of wave number k, these coefficients fall off rapid with order n, and the series is found to converge after a number of terms $n_c=(ka)+4.05(ka)^{1/3}+2$. For a micrometer-scale latex sphere in water, $n_c \leq 30$. The normalized image of an individual sphere can be fit to Eq. (1) for the sphere's position $r_p$, its radius a, and its refractive index $n_m$.

Although the scattering coefficients must be computed with great care [10, 11], the numerical challenge presented by Eq. (2) is in evaluating the vector spherical harmonics $M_{o1n}^{(3)}(k(r-r_p))$ and $N_{e1n}^{(3)}(k(r-r_p))$ at each pixel in $a(r)$ for each trial value of $r_p$. Each sphere's image can subtend tens of thousands of pixels, and the functions typically must be evaluated hundreds of times in the course of each nonlinear fit. Even with the best conventional computationally efficient formulations of the relevant special functions, a fully converged fit can take several seconds on a single processor.

One most preferred form of the invention concerns methods to accelerate these fits using the Lorenz-Mie technique combined with particular programming steps. As will be shown hereinafter this methodology reveals solutions to problems and enables commercially effective characterizations, wherein those solutions were not even previously available. One of our reference systems consists of micrometer-scale latex spheres freely diffusing in water at room temperature, whose normalized hologram is shown in FIG. 1C(1). We analyze images such as this with software developed in the IDL programming language (ITT Visual Information Solutions, Boulder, Colo.), taking advantage of the MPFIT suite of Levenberg-Marquardt nonlinear least-squares fitting routines. These fits typically yield the particle's in-plane position to within 3 nm, its axial position to within 10 nm, its radius to within 1 nm and its refractive index to within 1 part in $10^4$. Error estimates obtained from uncertainties in the fit parameters are independently confirmed by dynamical measurements.

Figure 2:
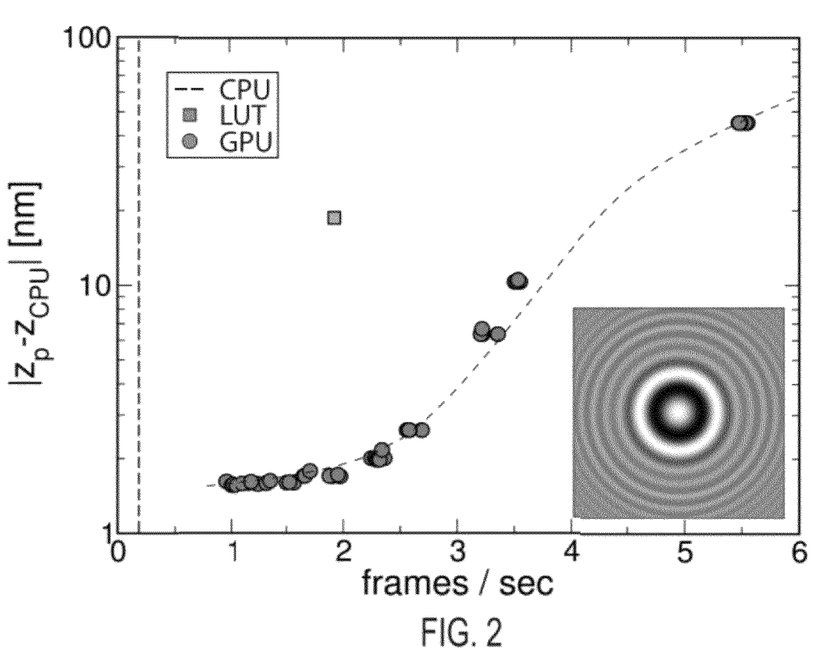
FIG. 2 shows processing speed and relative error in $z_p$ for fits, performed in accordance with the invention, to measured holographic images of a 2.2 μm diameter silica sphere using a one-dimensional look-up-table (squares) and single-precision GPU-accelerated fits (circles); the inset image shows a typical 201×201 pixel hologram and errors are computed relative to the double precision result obtained on a single-thread of the CPU (central processing unit), whose processing rate is indicated by the dashed line and the smooth curve is a guide to the eye.

Much of the computational burden of fitting Eq. (1) to a normalized holographic image can be relieved by evaluating $f_s(kR)$ along the line segment $R=|r-r_p|$ and then interpolating to obtain $f_s(k(r-r_p))$. This approach exploits the approximate radial symmetry of $a(r)$ about the particle's center. The data in FIG. 2 demonstrate the substantial reduction in processing time attained in this way. Although expedient, one-dimensional look-up tables do not account for slight polarization-dependent asymmetries in spheres' image, and can fail to capture rapidly varying features in $a(r)$. Consequently, results for the particle's position and characteristics obtained from interpolated fits differ slightly from reference value obtained with two-dimensional fits. Under circumstances where precision can be sacrificed for speed, the convergence tolerances on both one- and two-dimensional fits can be relaxed to obtain results with fewer optimization cycles. For instance, accepting tracking errors of 5 nm in plane and 20 nm in the axial direction yields a tracking rate for a 201×201 pixel image of 2 frames/s on a 3.2 GHz Intel Core 2 Duo processor, as shown in FIG. 2.

More substantial gains can be obtained by combining the Lorenz-Mie formalism with exploiting the parallel processing capabilities of a graphical processing unit (GPU) typically used in high-end computer graphics cards. Further detail concerning the GPU will be illustrated hereinafter in reference to FIG. 8 and the computer 200. Whereas conventional CPU-based implementations operate on each pixel in sequence, a GPU-enabled algorithm operates on all pixels simultaneously. We implemented a GPU-enabled computation of $f_s(kr)$ using the GPUlib (Tech-X Corp., Boulder, Colo.) extensions to IDL on an nVidia 280 GTX graphics card (nVidia Corp., Santa Clara, Calif.) installed in the host computer. GPUlib provides access to the underlying CUDA framework for mathematical computation on GPUs without requiring the sophisticated programming techniques typically required to implement mathematical computations on GPUs. With these enhancements, two-dimensional fits run with full precision at nearly 3 frames/s, a factor of 20 faster than CPU-based analysis. Accepting 5 nm in-plane resolution and 50 nm axial resolution yields particle tracking and characterization data at more than 5 frames/s, as shown in FIG. 2. The GPU, furthermore, supports multi-threaded operation. When supported by a multi-core CPU, this means that several analyses can proceed in parallel, yielding a proportional increase in total processing speed. This may be considered to be real-time performance in some applications. The meaning of "real time" is that image data from each frame snapshot of image data is available for processing and use before the net frame snapshot arrives. As will be noted hereinafter this allows real time characterization of a particle of a sample, such as for example, of a sample's position, radius and index of refraction, and molecular level coatings like bead based molecular binding features. At least two of these parameters can be determined at a time and can even be all simultaneously. Substantial further acceleration could be attained by implementing the same fitting algorithm in an optimized compiled programming language.

Even if fitting to a particle's image proceeds rapidly enough for real-time applications, analyzing a snapshot requires a preliminary identification of the particles of the sample 110 in the field of view, and starting estimates for the particle's position, size and refractive index that are sufficiently accurate for the fit to converge to the globally optimal solution. This bootstrapping process must be both fast and reliable if holographic analysis is to be useful for unattended automated processing.

Figure 3A:
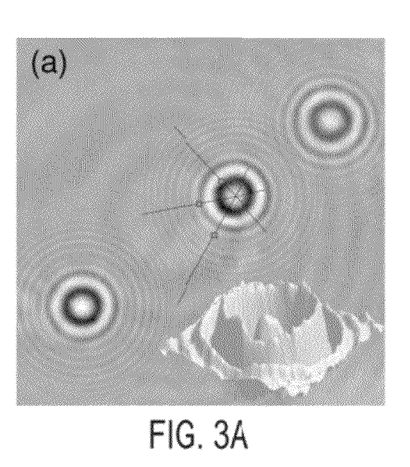
FIGS. 3A and 3B are, respectively, an original and transformed holographic images of three colloidal spheres; superimposed line segments in FIG. 3A indicate the "votes" cast by three representative pixels and intensity in FIG. 3B is scaled by the number of votes, with black representing 0 and white representing 800 votes and superimposed surface plots illustrate the middle sphere's transformation (Scale bar indicates 10 μm.)
Figure 3B:
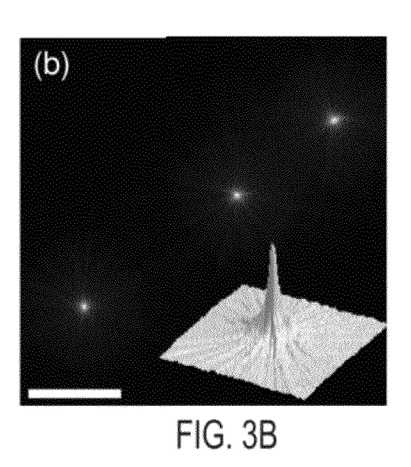

Each sphere appears in a snapshot, such as the example in FIG. 3A, as concentric bright and dark rings. The gradient of the intensity at each pixel therefore defines a line segment in the imaging plane along which a sphere's center may lie. The intersection of such lines defines an estimate for the particle's centroid in the focal plane. In the most preferred embodiment the particle is a sphere. We identify such intersections with a simplified variant of the circular Hough transform in which each pixel in the original image casts "votes" for the pixels in the transformed image that might be centroids. FIG. 3A indicates the votes cast by three representative pixels in the original image. The single-pixel votes are accumulated in a transformed image, such as the example in FIG. 3B. In this case, the transformed image has the same resolution as the original, a choice that yields both reasonable accuracy and speed. Those pixels in the transformed image with the most votes are taken to be centroid candidates, and their locations used as the in-plane coordinates to initialize fits. The inset surface plots demonstrate how the extended interference pattern due to a single sphere is transformed into a sharply defined peak, even if two or more spheres' holographic images overlap. This methodology is more computationally efficient than the conventional circular Hough transform, which uses additional resources to record information about each potential circular region's radius. Refining the centroid estimate by computing the brightness-weighted center of brightness for each feature in the transformed image typically identifies particles' centroids to within a few tenths of a pixel, or a few tens of nanometers.

Having estimated a particle, or sphere's, in-plane coordinates, we then estimate its axial coordinate by back-propagating the measured light field using the Rayleigh-Sommerfeld propagator. Peaks in the reconstructed axial intensity correspond with particle positions to within 100 nm, even when particles occlude each other along the optical axis. This back-propagation can be performed with a one-dimensional slice of image data, centered on the particle's position, and therefore can be performed very rapidly.

Figure 4:
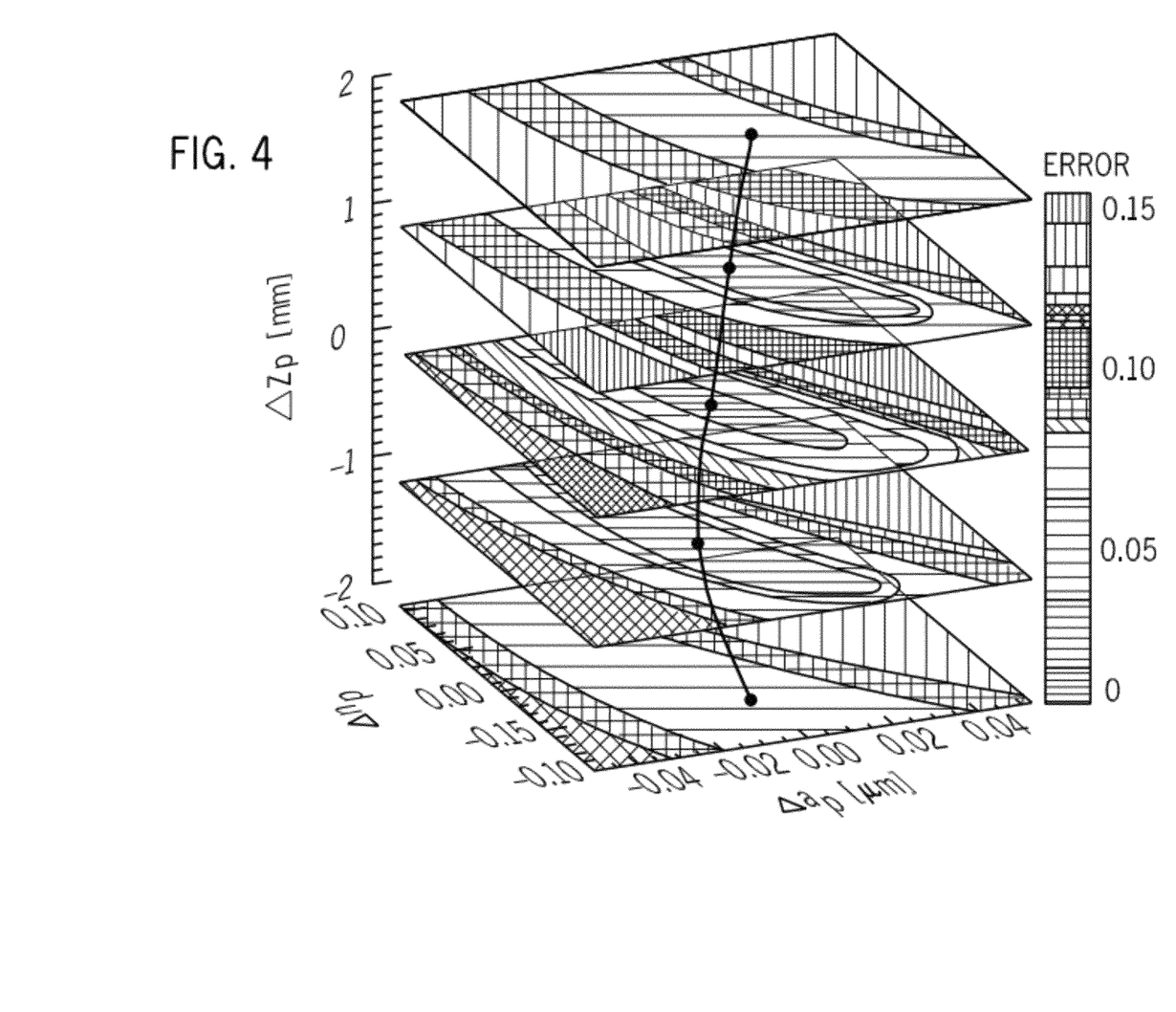
FIG. 4 show the root-mean-square error in the hologram estimated for a 1.5 μm diameter silica sphere in water as a function of the error in radius, $\Delta a_p$, refractive index, $\Delta n_p$, and axial position $\Delta z_p$, where the curve indicates the path of minimum error parameterized by $\Delta z_p$.

Accurately estimating the size and refractive index of an unknown particle is substantially more difficult. Fortunately, the error surface for the nonlinear fits slopes smoothly and monotonically toward the globally optimal values over a very large catchment basin in the parameter space defined by $a_p$, $n_p$, and $z_p$. FIG. 4 shows the root-mean-square error in the local image intensity computed for a 1.5 mm diameter silica sphere in water at $z_p=20$ mm, as a function of $\Delta a_p$, $\Delta n_p$ and $\Delta z_p$, errors in the radius, refractive index and axial position of the particle, respectively. These data demonstrate that fits to such a particle's image should converge to the optimal values even if the initial estimates are in error by more than 0.1 in the refractive index, 0.5 mm in the radius and 2 mm in the axial position. The error surface becomes more highly structured, and thus less forgiving, if the estimated in-plane centroid is in error by more than a hundred nanometers or so. Fortunately, the voting algorithm routinely yields sufficiently accurate results to ensure robust convergence. Tracking a particle through a sequence of images can be further accelerated by using the results from one fit as the initial estimates for the next. In this case, no additional pre-fitting is required.

The combination of rapid centroid identification and accelerated image fitting yields accurate and highly precise measurements of colloidal spheres' positions and characteristics in near or in real time as described hereinbefore. Unattended holographic particle tracking and characterization should find numerous applications in process control and quality assurance as well as in high-throughput and combinatorial assays. Substantial further acceleration should be possible through more aggressive software optimization and parallelization, without recourse to exotic hardware solutions.

Figure 5A:
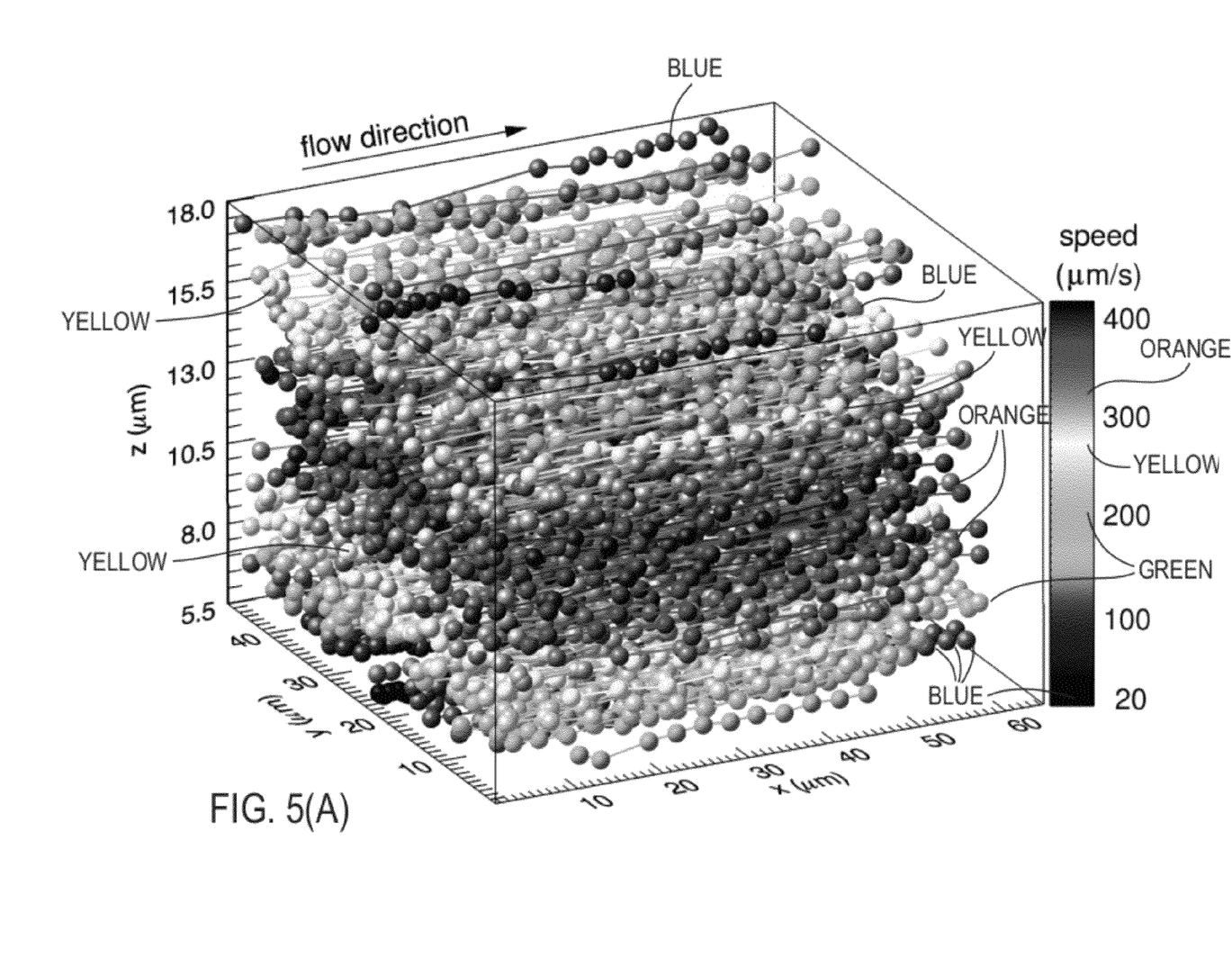
FIG. 5A shows holographic particle image velocimetry measured through dimensional trajectories of 500 colloidal spheres traveling down a microfluidic channel in a pressure driven flow with each sphere representing the particle position in one field of a holographic snapshot and features from field sequences are linked into trajectories with gray scale showing a range of particle measured speeds.

Holographic particle tracking has immediate applications for three-dimensional particle image velocimetry. FIG. 5A shows an example in the form of the superimposed trajectories of 500 individual one micrometer-diameter polystyrene spheres (Duke Scientific, catalog number 5100A) travelling down a 2 cm long microfluidic channel of 100 μm width and 17 μm depth. The spheres were dispersed in water at a volume fraction of $10^{-5}$, and were advected by a pressure-driven flow of water created by raising a reservoir against gravity. Images were obtained in a 50×70 μm² area near the middle of the channel, with the focal plane set roughly 5 μm below the lower glass/water interface. Spheres' locations in each snapshot are linked with a maximum-likelihood formalism approach into single-particle trajectories, $r_p(t)$, sampled at 1/60 s intervals. Not every time step is represented in each particle's trace because faster-moving particles near the mid-plane of the flow occasionally obscure slower-moving particles near the walls. FIG. 5A presents only those particle positions that were identified unambiguously. Even such incomplete time series can be used to estimate the particles' instantaneous velocities. The traces in FIG. 5A are of a gray scale according to the trajectory-averaged speed.

Figure 5B:
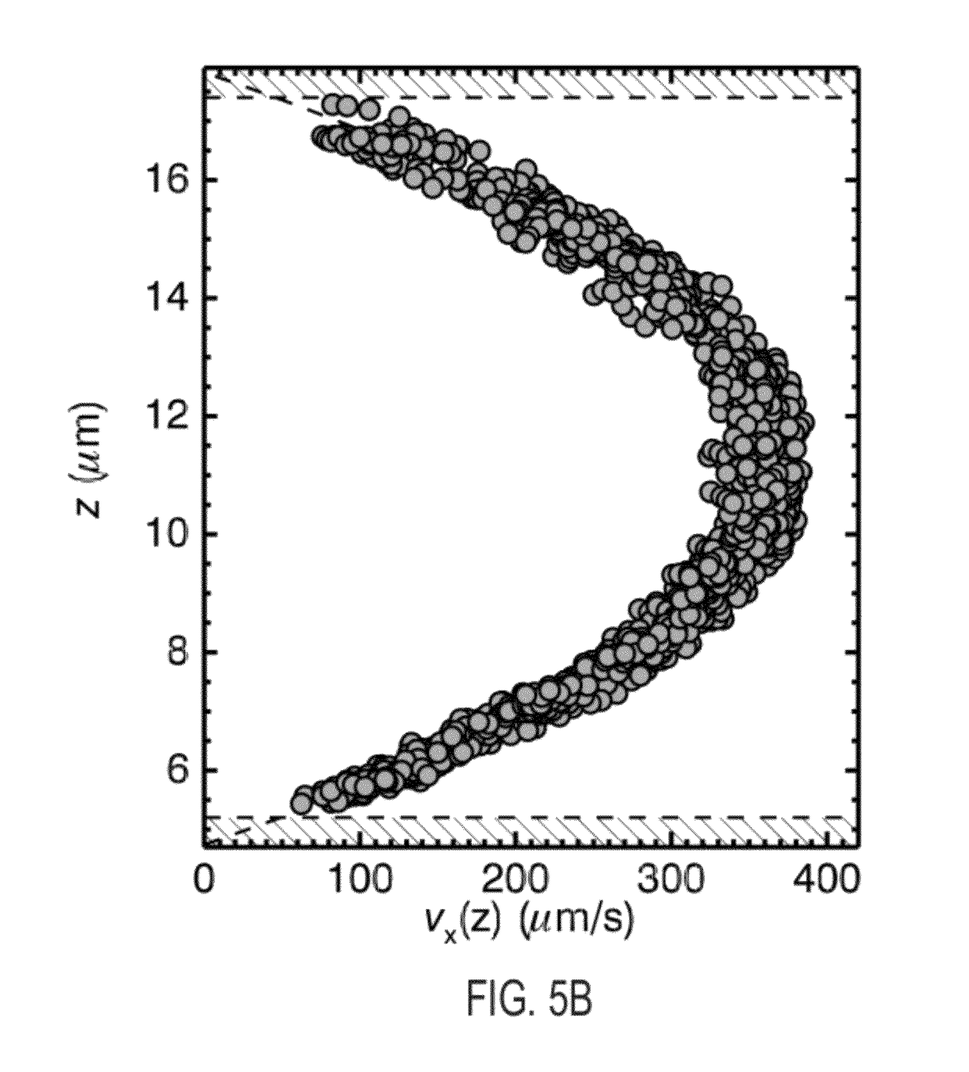
FIG. 5B shows a Poiseuille flow profile along the vertical direction attained from FIG. 5A data with particles excluded from the shaded region by interactions with upper and lower glass walls of the channel (the dashed curve is a fit to the anticipated parabolic flow profile)

These trajectories also are useful for mapping the three-dimensional flow field. Each point in FIG. 5B represents one particle's speed as a function of its mean height, z, in the microfluidic channel. The superimposed results of 1000 such trajectories clearly show the parabolic flow profile expected for Poiseuille flow down a channel, the width of the cluster of data reflecting spatial variations across the long horizontal axis of the channel. The limits of the vertical axis indicate the positions of the channel's upper and lower walls, with heights being reported relative to the microscope's focal plane. The dashed horizontal lines represent the region of the flow into which particles cannot wander because of their hard-sphere interaction with the glass walls. The fit parabola shows the flow vanishing at the channel's boundaries.

Figure 6A:
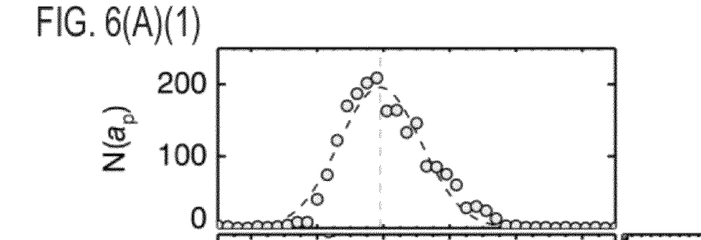
Figure 6B:
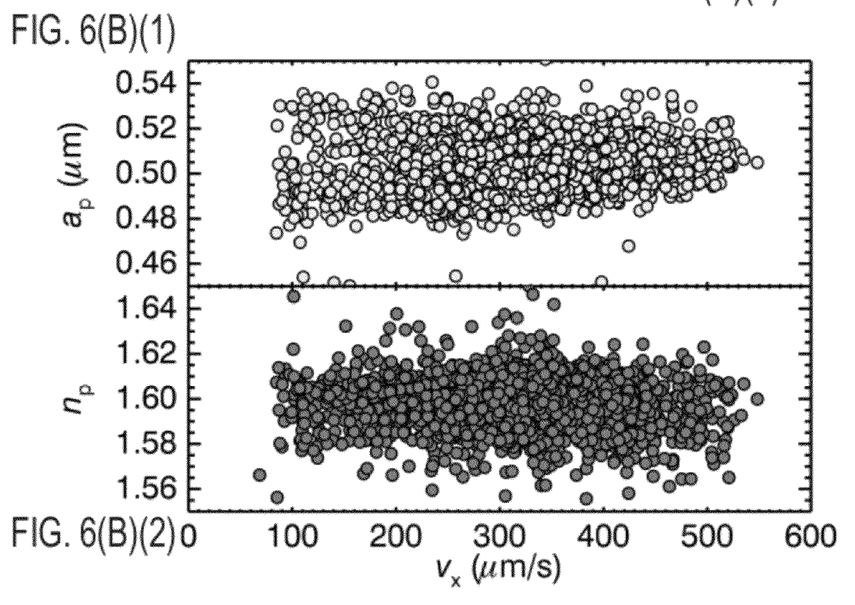

Each trajectory also yields trajectory-averaged measurements of the radius and refractive index for each particle individually. Combining multiple measurements on a single particle minimizes systematic errors due to inevitable position-dependent variations in the illumination. The results in FIG. 6A(1)-A(3) show the radii and refractive indexes of the spheres in a commercial sample of polystyrene microspheres dispersed in water. FIGS. 6A(2) and A(3) show the 2D histograms taken from FIG. 6A(1). The mean radius of $a_p=0.4995$ μm agrees with the manufacturer's specification obtained by conventional light scattering, as does the measured 2.5 percent polydispersity in the radius. The mean refractive index of $n_p=1.595$ is consistent with independent measurements on polystyrene spheres.

Single-particle characterization is a substantial benefit of holographic characterization compared with bulk light-scattering measurements, which are the usual basis for analyzing particle dispersions. Building up distributions such as the example in FIGS. 6A(1)-A(3) from single-particle measurements eliminates the need for population models, and thus affords more general insights into a sample's composition. For example, the anticorrelation between the particles' size and refractive index evident in FIGS. 6A(1)-A(3) would not be apparent in light scattering data. No such anticorrelation is apparent in holographic analyses of homogeneous fluid droplets. One interpretation of this observation is that the larger spheres in the emulsion polymerized sample are more porous, and consequently have lower refractive indexes.

Simultaneously tracking and characterizing individual particles (and in real time as described hereinbefore) enables us to confirm our results' freedom from motion-based artifacts. Colloidal particles' images become blurred if they move during the period that the camera's shutter is open. This blurring introduces substantial artifacts into conventional bright-field video microscopy data. As the results in FIGS. 6B(1) and B(2) demonstrate, however, motion blurring has no discernible influence on values for the radii and refractive indexes as a function of mean speed obtained by holographic analysis for speeds as high as 500 μm/s. Additional measurements reveal deviations from the population average values only for peak flow speeds exceeding 700 μm/s.

This robustness is surprising because particles travelling at several hundred micrometers per second traverse several of our camera's pixels during its 1 ms shutter period. The resulting incoherent average of the oscillatory scattering pattern serves primarily to reduce the contrast in the direction of motion, however, and so has little influence on the Lorenz-Mie fit. Even this amount of blurring could be reduced through the use of a faster shutter or a pulsed laser for illumination.

Being able to characterize individual colloidal particles in real time as they travel down a microfluidic channel provides an effective basis for detecting molecular-scale coatings on functionalized beads. If the individual spheres' radii were known to within a nanometer or so, then the presence of a molecular coating of similar refractive index could be discerned in the apparent increase in the radius. More generally, the characteristics of a treated sample can be compared with control measurements on untreated spheres.

Figure 7A:
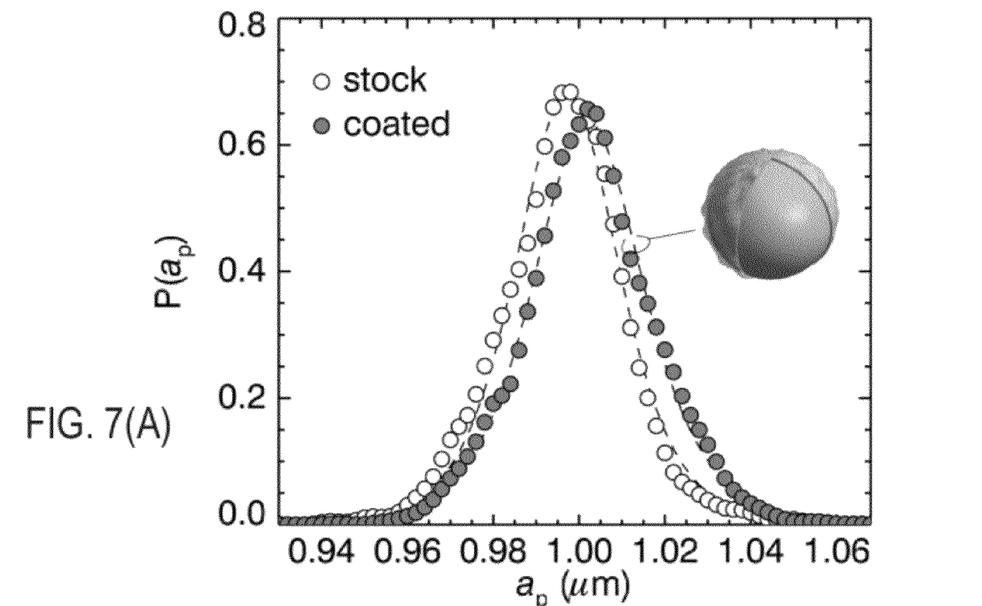
FIG. 7A shows detection of avidin binding to biotinylated polystyrene spheres with light circles the probability distribution for measured particle radius in stock spheres with dark circles having a corresponding distribution for a sample of the sphere after incubation with neutravidin (dashed curves are guides for the eye)
Figure 7B:
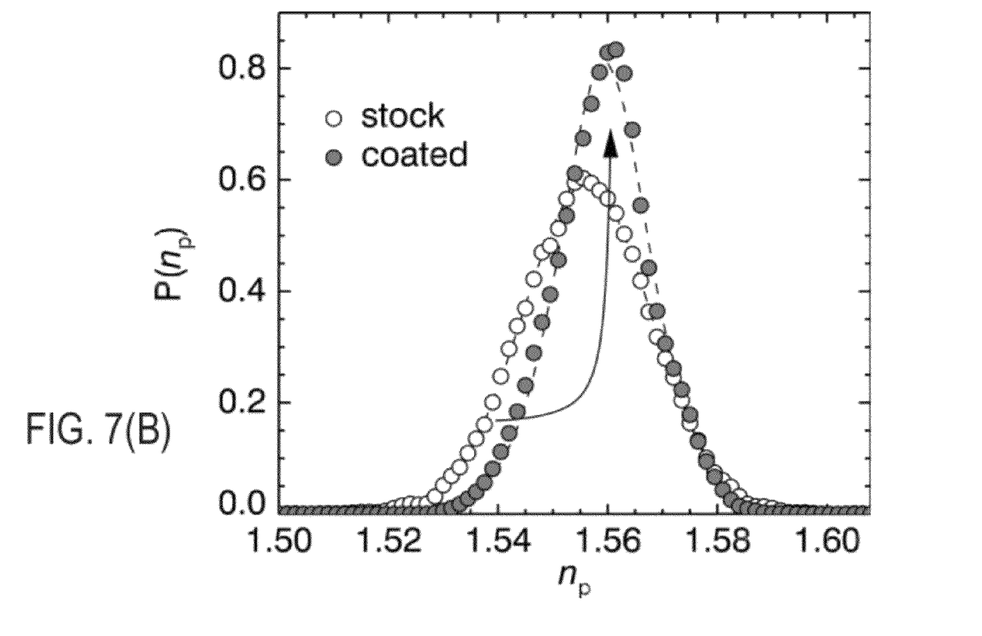
FIG. 7B is the equivalent distribution for particles' refractive indices with the arrow indicating redistribution of probabilities from a low density tail in a stock sample to the peak in the coated sample.

FIGS. 7(A) and 7(B) shows one such comparative example study of 2 μm diameter biotinylated polystyrene spheres before and after incubation with neutravidin. The biotinylated polystyrene spheres used in this study were obtained from Polysciences Inc (Warrington, Pa.) (catalog number 24172). Neutravidin was obtained from Invitrogen (Carlsbad, Calif.) (catalog number A2666). A neutravidin solution at a concentration of 1 mg/mL was prepared by adding 1 mg of neutravidin to 1 mL of phosphate buffer saline (PBS) (50 mM, [NaCl]=50 mM). The stock sample of beads was obtained by adding 10 μL of the as-delivered dispersion to 990 μL of PBS. The coated sample was prepared by adding 10 μL of the as-delivered dispersion to 990 μL of neutravidin solution. Particles were incubated and shaken at room temperature for 1 hr before they were introduced into the microfluidic channels by capillary action. Flow was induced by introducing a slip of absorbent paper into one end of the channel and images recorded until results were obtained for 1,000 spheres from each sample. Each data set consisted of roughly 5,000 holographic measurements, which were obtained over the course of roughly 5 min.

From these measurements, we determined that the untreated sample has a population averaged radius of 0:996±0:015 μm (see FIG. 7A), consistent with the manufacturer's specification. The incubated population appears to some 6 nm larger, with an average radius of 1:002±0:015 μm. Even though the two size distributions plotted in FIG. 7A overlap substantially, a Wilcoxon rank-sum test demonstrates that their means differ with better than 99 percent certainty. This then constitutes a statistically significant detection of change in the treated sample's radius, which can reasonably be ascribed to the presence of a molecular-scale coating. The coating's thickness, in this case, is consistent with the size of a multi-domain avidin derivative.

Pronounced differences between the two samples also are evident in the measured distribution of refractive indexes, plotted in FIG. 7B. The incubated sample's distribution is significantly sharper, presumably because protein, whose refractive index is similar to that of polystyrene, displaces water in the spheres' porous surfaces, and raises their effective refractive indexes. This would affect the more porous particles on the lower side of the refractive index distribution more than the denser particles on the high side, thereby sharpening the distribution. The arrow in FIG. 7B indicates this redistribution.

Similar analyses of random samples of the two data sets further confirm that the particles from the untreated sample all come from the same population, whose size and refractive index is consistent with the manufacturer's specification. The treated samples, by contrast show more variability in size, possibly because the thickness and evenness of the bound avidin layer can vary from sphere to sphere.

These results demonstrate the utility of hardware-accelerated digital video microscopy for detecting in real time molecular-scale coatings on functionalized colloidal spheres. Unlike conventional molecular binding assays, holographic analysis does not require fluorescent or radiological markers, and so eliminates the effort and expense ordinarily required to label molecules bound to beads.

Figure 8:
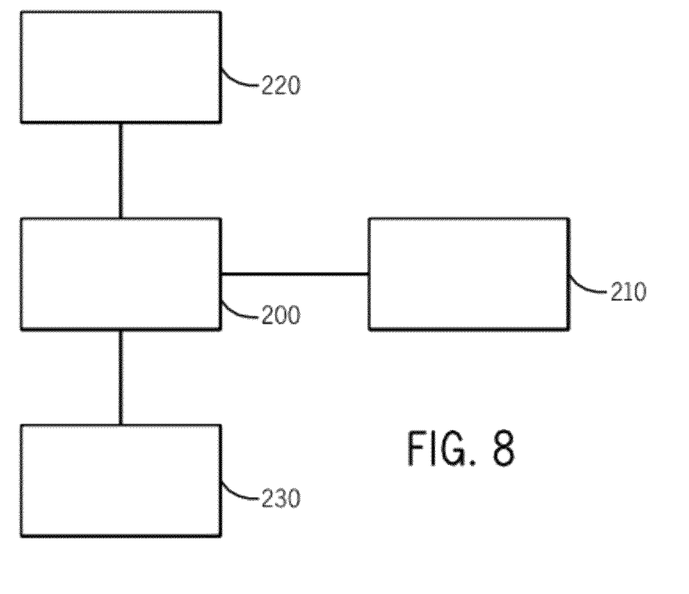
FIG. 8 shows a schematic block diagram of a computer system for implementing the methods of the invention.

In one embodiment of the invention the method of the invention can be implemented to determine parameters and features of interest by use of the computer system shown in FIG. 8. The system of FIG. 8 includes a computer 200 (which can include a CPU and/or GPU in a most preferred embodiment as described herein in connection with Lorenz-Mie analysis) which can execute a computer readable medium, such as a computer software module with instructions which are embedded, for example, in a computer addressable storage medium 210. The use of the GPU in the computer 200 thereby allows real time analysis and simultaneous evaluation of parameters such as molecular coatings and/or of a particle's position, radius and index of refraction. This storage medium 210 can be read/writeable which enables data to be written thereto. This feature allows subsequent static or dynamic data analysis; and results of that analysis allow a user to act on that information for advantageous applications. The computer 200 executes the computer software module instructions to analyze data produced by the previously described methods of the invention. Such data can be obtained from the storage medium 210 and input via device 220. Other conventional devices, such as an output device 230 (e.g., a display, printer and/or a storage medium) can enable viewing and further data analysis. Such analysis can yield information about the position and characteristics of particles in real time or delayed time.

Certain embodiments described hereinbefore use holographic video microscopy in a single wavelength to detect molecular-scale coatings on micrometer-diameter dielectric colloidal spheres. This detection was accomplished by analyzing a population of spheres that had been exposed to the coating molecules and comparing the results with those obtained by analyzing a comparable population of spheres that had not been exposed. Holographic snapshots of individual spheres in each population were analyzed with the Lorenz-Mie theory of light scattering to obtain estimates for the sphere's radius and complex refractive index. Lorenz-Mie analysis yields each sphere's radius with nanometer resolution and its refractive index to within a part in a thousand. The systematic differences in the population distributions of these properties constitute the basis for detecting the molecules. Coated spheres appear systematically larger by an amount consistent with the thickness of the coating.

In an alternative embodiment, the Lorenz-Mie analysis can employ two-color or multi-color holograms to provide comparable detection resolution using only a single sphere, rather than populations of spheres. Thus the input beam 120 in FIG. 1A provides an output of a multi-color hologram. This embodiment creates simultaneous holographic images in two or more wavelengths. These multi-color holograms can be recorded on separate video cameras 135 (see FIG. 1A) using filters to separate the images. Alternatively, they can be recorded with a color camera 135, and the separate images obtained from the recorded color channels.

The spheres used for these types of measurements should have comparable optical properties in the wavelengths used. The coating, however, should have strongly differing properties in at least two of the wavelengths. For instance, the coating might be a pure dielectric in one wavelength and strongly absorbing in another. In the absence of a coating, holograms obtained in multiple wavelengths should yield identical results for the particle's position and size. Coated spheres' holograms should differ significantly in the estimated size and in the qualitative features of the estimated refractive index obtained from each wavelength. Such differences would constitute a detection of the molecular-scale coating. Suitable choice of wavelength, sphere size and sphere composition should provide quantitative information on the thickness or completeness of the coating.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

What is claimed is:

1. A method of characterizing a parameter of a sample by holographic microscopy, comprising the steps of:
   providing holographic image data of the sample from a storage medium;
   determining a first estimate of the number of objects in the holographic image data, each object associated with a set of concentric bright and dark rings;
   determining, for each set of concentric bright and dark rings, by a voting algorithm, a centroid defined by an approximate x, y position in a plane, with each pixel of the image data voting for pixels in a transformed image that may be centroids;
   determining an estimate of the axial position (z) of each of the objects;
   determining by Lorenz-Mie analysis an estimate of each of the objects' radius, refractive index;
   using holographic image data from the sample to characterize properties of the sample and generate information characteristic of the parameters of the sample; and
   analyzing the information characteristic of the sample parameters and determining in real time simultaneously size, position and refractive index of a particle of the sample.

2. The method as described in claim 1 wherein the step of providing the image data includes generating a polarized light beam and scattering the light beam off the sample, to generate a hologram.

3. The method as defined in claim 1 wherein parameter characterization includes the steps of determining bead based molecular binding features.

4. The method as defined in claim 1 wherein parameter characterization includes automatic particle detection.

5. The method as defined in claim 1 wherein determining the centroid further includes determining the Lorenz-Mie functionality scattering function $f_s(kr)$ along a line segment $R=|r-r_p|$ and interpolating to obtain a function $f_s(k(r-r_p))$ thereby reducing processing time and providing real time analysis of the sample.

6. The method as defined in claim 5 wherein the sample comprises a particle and the Lorenz-Mie analysis method determines in real time at least one of the size, shape, composition and orientation of the particle.

7. The method as defined in claim 6 wherein the particle comprises a sphere, thereby enabling real time determination of rapidly varying features of particle radius.

8. The method as defined in claim 1 wherein the polarized light beam comprises a single wavelength for the light.

9. The method as defined in claim 1 further including the steps of performing the Lorenz-Mie analysis and obtaining comparisons between of the image data a particle being in an untreated state and another particle having undergone a treatment, thereby enabling real time characterization of molecular layers present on the treated particle versus the untreated particle.

10. The method as defined in claim 9 wherein the real time characteristics are selected from the group of index of refraction and particle radius.

11. The method as defined in claim 1 further including the step of estimating in-plane co-ordinates of the particle by the Lorenz-Mie analysis and then estimating axial coordinate of the particle by back-propagating the measured light field applying a Rayleigh-Sommerfeld propagator.

12. The method as defined in claim 1 wherein the analysis step includes applying a Levenburg-Marquardt fitting routine to identify the in-plane co-ordinate within 3 nm.

13. The method as defined in claim 1 further including the steps of determining velocity of the particle in a flowing form.

14. The method as defined in claim 13 further including the step of mapping a three-dimensional flow field of the particle.

15. The method as defined in claim 13 wherein the step of analyzing the information comprises simultaneously tracking and characterizing individual ones of the particles, thereby avoiding motion induced artifacts of the characteristics of the particles.

16. The method as defined in claim 1 wherein the step of measuring includes identifying molecular-scale coatings on functionalized forms of the particle by detecting variations in apparent increase in radius.

17. A method of characterizing parameters for holographic microscopy of objects comprising the steps of:
   receiving image data from a storage medium;
   transforming the image data using a Hough circular transform to determine by a voting algorithm a first estimate of the number of objects in the image data and the objects approximate x, y position in a plane;

using the transformed data to determine a first estimate of the axial position (z) of each of the objects along with a first estimate of each of the object's size and composition; and applying Lorenz-Mie analysis of the image data for each of the objects to determine a second estimate of the resolution position, size and composition of each of the objects, wherein the second estimate has a higher accuracy than the first estimate with at least one step of updating the storage medium with the results and providing the results for display for interpretation by a user.

18. The method of claim 1, wherein the determination of a centroid is by application of a circular Hough transformation wherein each pixel in an original image votes for the pixels in a transformed image.

* * * * *